United States Patent [19]
Herrig et al.

[11] Patent Number: 5,458,566
[45] Date of Patent: Oct. 17, 1995

[54] RESERVOIR VOLUME SENSING SYSTEMS FOR AUTOLOGOUS BLOOD RECOVERY

[75] Inventors: Russell L. Herrig, Sharon; Joseph R. Plante, Millis; Frank J. Anderson, Mansfield; Paul M. Volpini, Quincy; Norbert J. Comeau, Marshfield, all of Mass.

[73] Assignee: Haemonetics, Inc., Braintree, Mass.

[21] Appl. No.: 36,430

[22] Filed: Mar. 24, 1993

[51] Int. Cl.⁶ .................................................. A61M 37/00
[52] U.S. Cl. ............... 604/4; 73/862.634; 128/DIG. 13; 604/29; 604/31
[58] Field of Search .................. 422/44, 45; 73/862.627, 73/862.634, 862.636, 862.639, 862.338; 604/4–6, 29, 31; 128/DIG. 13, DIG. 6

[56] References Cited

U.S. PATENT DOCUMENTS

| | | | |
|---|---|---|---|
| 2,705,493 | 4/1955 | Malmros et al. | 128/214 |
| 2,847,008 | 8/1958 | Taylor et al. | 128/214 |
| 2,927,582 | 3/1960 | Berkman et al. | 128/214 |
| 4,231,366 | 11/1980 | Schael | 128/214 |
| 4,458,539 | 7/1984 | Bilstad et al. | 604/6 |
| 4,466,804 | 8/1984 | Hino | 604/4 |
| 5,141,493 | 8/1992 | Jacobsen et al. | 604/29 |
| 5,337,618 | 8/1994 | Porcari et al. | 73/862.634 |

FOREIGN PATENT DOCUMENTS

| | | |
|---|---|---|
| 873801 | 7/1961 | United Kingdom . |
| 89/01792 | 3/1989 | WIPO . |
| 93/01858 | 2/1993 | WIPO . |

OTHER PUBLICATIONS

"Load Cell" Brochure, BLH Electronics, Inc. Feb. 1971 Bulletin 401–4 pp. 1–42.
Owner's Operating and Maintenance Manual: Cell Saver HaemoLite 2.
One page Operating Instructions: Haemonetics Cell Saver Collection Reservoir List No. 200.

Primary Examiner—Randall L. Green
Assistant Examiner—Rob Clarke
Attorney, Agent, or Firm—Cesari and McKenna

[57] ABSTRACT

A volume sensor is described for automating an extracorporeal system used for the recovery and concentration of salvaged blood. The system includes a disposable plastic reservoir in which blood is collected from the surgical site and stored for processing. Volume is sensed in one embodiment by a strain gage device which is sensitive to vertical forces. In another embodiment volume is sensed by measuring the transit time of an ultrasonic pulse-echo signal generated by piezoelectric transducer.

8 Claims, 5 Drawing Sheets

5,458,566

RESERVOIR VOLUME SENSING SYSTEMS FOR AUTOLOGOUS BLOOD RECOVERY

BACKGROUND OF THE INVENTION

As a patient loses blood during surgery, the blood is often replaced by transfusion to the patient. Conventionally, this requires that a supply of blood be available that is crossmatched with the patient's own blood to be certain that the two are compatible. The problems of processing blood from donors, of storing that blood and of crossmatching that blood with the patient are substantially circumvented by the use of autologous blood transfusion techniques. By such a technique, the patient's own blood, lost through a wound or surgical incision, is collected and returned to the patient.

Typically the patient's blood is collected from the surgical site by a suction wand. The collected blood may be contaminated by bone particles, fat, saline irrigation solutions and the like. To prevent return of those contaminants to the patient, the autologous transfusion systems clean the blood by separating out the components and contaminants in the centrifuge, concentrating the red blood cells, and washing the red blood cells in the centrifuge. The washed red blood cells are then returned to the patient.

Prior to delivery to the cell salvage system, the blood taken from the patient is collected in a reservoir. Typically that reservoir is a transparent, rigid plastic sterilized disposable container having a filter therein. The reservoir is connected at one end to a vacuum source and at the other end to the suction wand. The blood is suctioned into the reservoir through one or more input ports located at the top of the reservoir and is delivered to the cell salvage system through an outlet port at the bottom. A filter element is positioned between the inlet and outlet to remove bone fragments and the like from the blood.

Current operating procedures for autologous blood recovery systems required the operator to visually monitor the volume of blood fluid as it is collected by the suction wand and stored in the reservoir. The operator then initiates the cell salvage process when sufficient volume of blood is observed to be present in the reservoir. When this volume is processed the cell salvage process is stopped. The operator must then wait and observe the volume level of blood collected by the wand into the reservoir and reinitiate processing when the predetermined level is obtained. A need exists for automating this time-consuming procedure and to eliminate the human factor which requires the diligence of a user to watch the reservoir volume to prevent overflow.

DETAILED DESCRIPTION OF THE INVENTION

System Description

Figure 1:
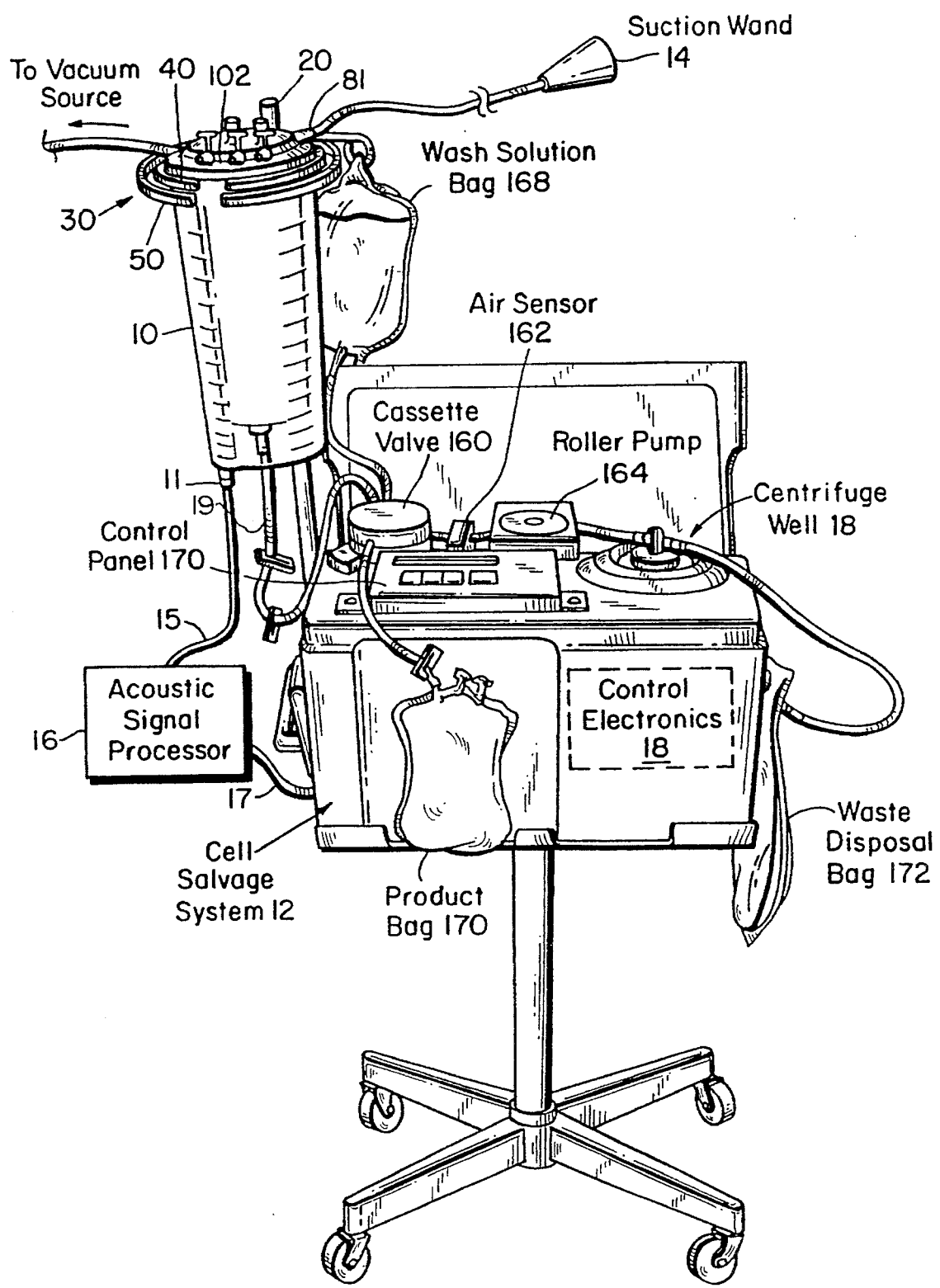
FIG. 1 is a perspective view of the system of the invention.

Referring now to the drawings of FIG. 1 and FIG. 2 a reservoir volume sensing system for autologous blood recovery will now be described in connection therewith.

Reservoir 10 is a tubular plastic transparent disposable reservoir for temporarily storing body fluids aspirated by suction wand 14 from a surgical or post recovery patient site. Vacuum for wand 14 is supplied by vacuum source (not shown) which is connected through port 130 in cover 102 of reservoir 10 to the suction wand 14 via one or more redundant ports 81. In a first embodiment of the invention the volume of fluid in the reservoir is sensed by an external strain gage transducer assembly 30 (See FIGS. 2–4) mounted between pole/stand 20 and reservoir 10. An electrical signal, indicative of fluid weight W is generated by assembly 30 and coupled by an electrical lead 9 (see FIG. 4) to cell salvage control electronics (18) in cell salvage system 12. In an alternate embodiment the height H of fluid in the reservoir is sensed by an ultrasonic sensor 11, coupled to the bottom of the reservoir 10, using a pulse echo detection method. An electrical signal (proportional to H) is generated by the sensor 11 and is coupled by lead 15 to a processor circuit 16. Processor 16 calculates the time delay between a transmitted ultrasonic pulse and its received echo. This time delay is directly proportional to the fluid height H. A digital value representative of this time is then transmitted to the cell salvage control electronics (18) over leads (17).

Note: The ultrasonic implementation has an integral microprocessor circuit 16 that processes the signals and extracts information to feed to cell salvage Control Electronics 18 (also microprocessor-based). The strain gage embodiment does not have a first computer processing stage. It interfaces directly to the Cell Salvage Control electronics.

In either alternative embodiment, the control electronics 16 uses the information to control the operation of cell salvage system 12. Cell salvage system 12 is in fluid communication with the fluid in reservoir 10 via tubing 19. Cell salvage system 12 utilizes the volume information to automatically initiate processing by peristaltically pumping fluid with roller pump 164 from reservoir 10 when sufficient volume of blood fluid is present in the reservoir 10 as sensed by either the strain gage sensor 30 or the ultrasonic sensor 11.

Cell salvage system 12 is a modified revision of the Cell Saver® Haemolite® 2 system made by Haemonetics®Corporation and is generally described in U.S. Pat. No. 4,946,434 (incorporated herein by reference). In the system 12 a disposable manifold cassette valve 160 is used to couple fluids from reservoir 10 and wash solution bag 168 to or from centrifuge 18 product bag 170 and waste disposal bag 172 under the control of electronics 18.

The system can accurately and repeatably determine reservoir volume without being significantly affected by normal clinical conditions including reservoir tilting, collected blood composition, blood collection rate, or fluid turbulence. The volume measurement is continuous over a predetermined range. The volume at which processing is initiated or resumed is programmable and software in the computer may be programmed with logic to decide when processing should be initiated or resumed depending on the state of the process and the size of the processing chamber.

The system of the invention is capable of:
1. Providing a continuous measurement of reservoir fluid volume without direct contact with the reservoir (fluid) contents.
2. Determining fluid volume despite unpredictability and nonhomogeneity of fluid contents with respect to hematocrit, cellular composition, fat, bone particulate, and miscellaneous other material which may be collected from a surgical site.
3. Determining fluid volume under a range of clinical conditions including flow rate of incoming fluid, reservoir tilting, fluid turbulence, and air bubbles suspended in the fluid.

4. Resolving reservoir volume over a target center range (e.g. 100 to 2000 ml to within 100 ml).
5. Detecting and differentiating the conditions when the reservoir volume is below or above the measurement range. (Ultrasonic implementation only.)
6. Detecting whether the sensor cable and sensor is electrically connected to cell processing equipment.
7. Detecting whether the sensor is properly mechanically coupled to the reservoir. (Ultrasonic implementation only.)
8. Allowing the user to modify volume setting at which processing is initiated.
9. Allowing connection of the sensor to the reservoir with power "on" or "off" to the system.

Strain Gage Embodiment

Figure 2:
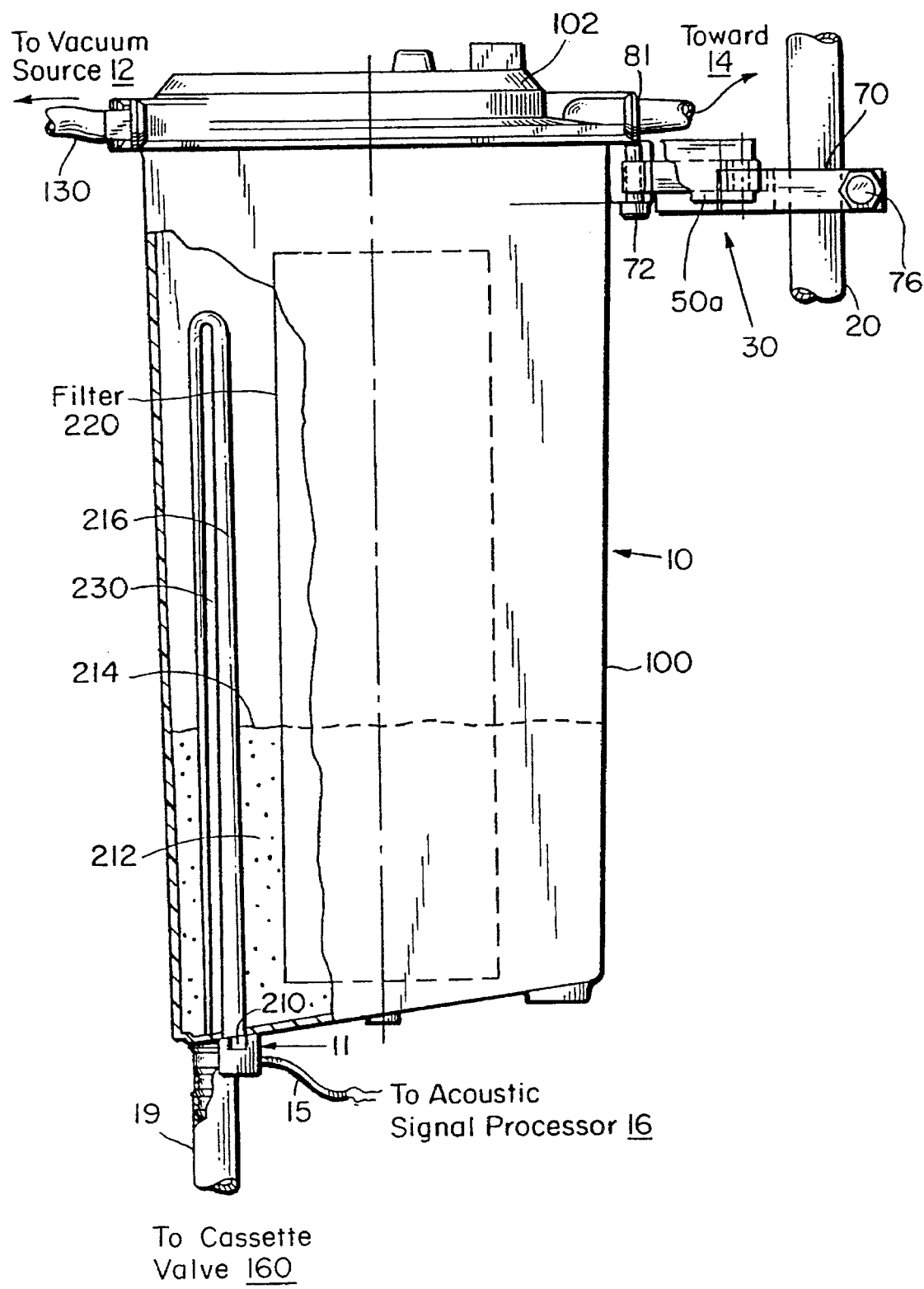
FIG. 2 is a partly broken away side-view of the reservoir of FIG. 1 of the invention.
Figure 3:
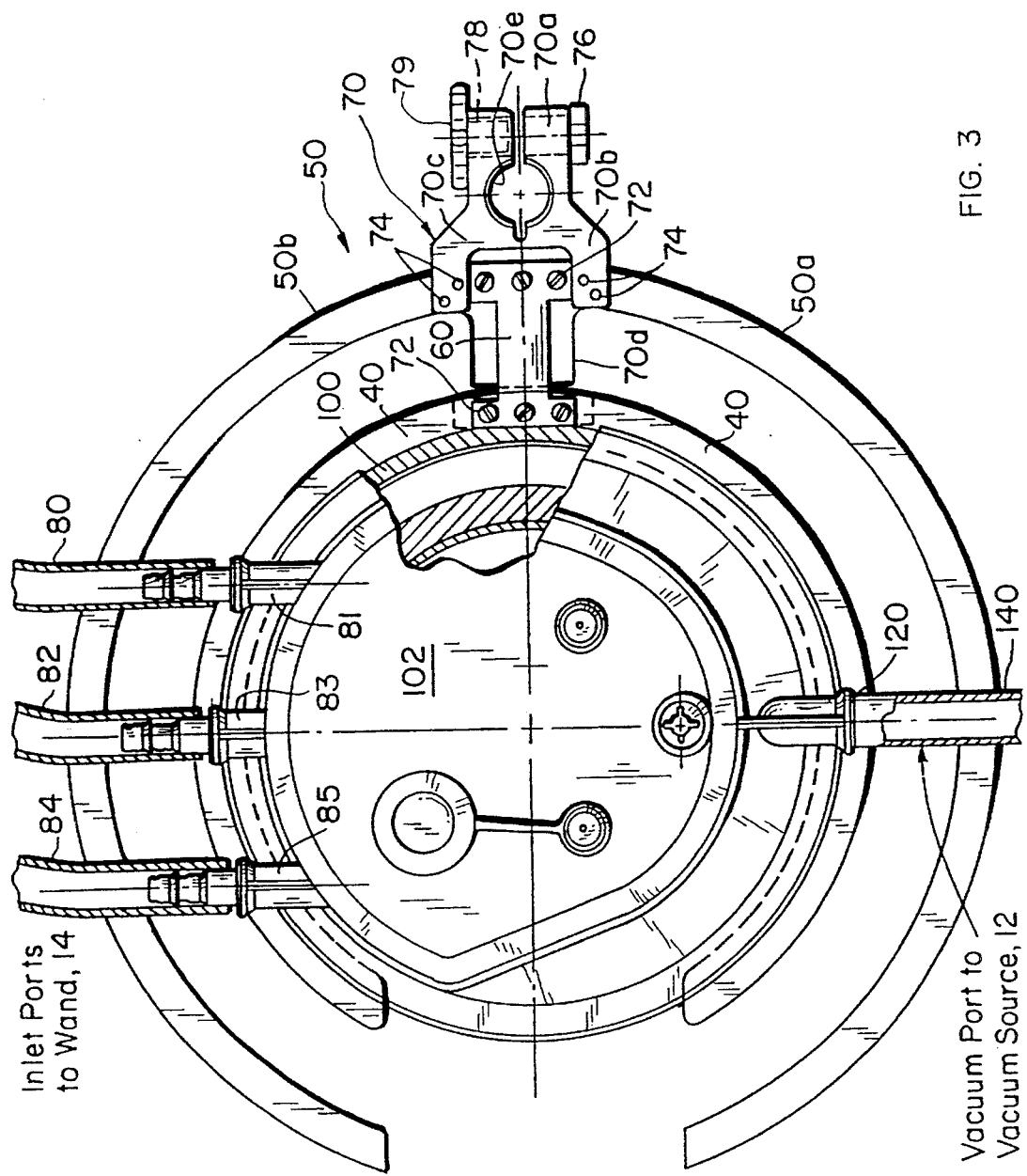
FIG. 3 is a partly broken away top-plan view of the FIG. 2 embodiment.
Figure 4:
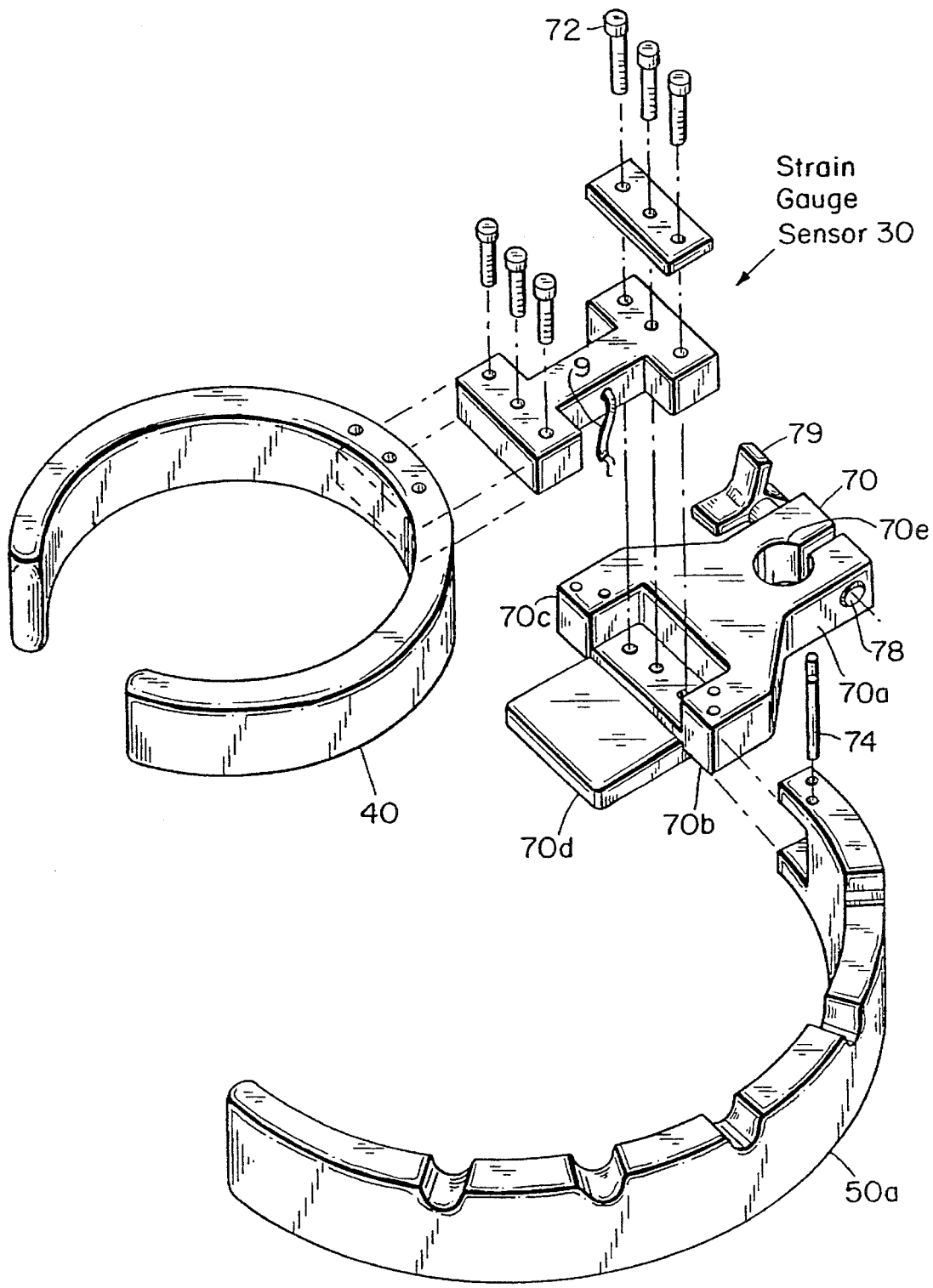
FIG. 4 is an exploded perspective view of the strain gage assembly 30 of FIG. 2.

Referring now to FIGS. 2–4 a strain gage embodiment of the volume sensor will now be described in detail in connection therewith. A reservoir 10 for collecting aspirated fluids from a patient during surgical and postoperative periods is suspended from an IV pole stand 20 by a strain gage assembly 30 shown in detail in FIG. 4.

Note that for convenience reservoir 10 has been modified to include an ultrasonic sensor embodiment. However, it is to be understood that preferably the strain gage sensor would be utilized with a standard unmodified reservoir such as the Haemonetics® Cell Saver® Collection Reservoir List No. 200.

Assembly 30 consists of an inner reservoir split-ring 40; an outer reservoir split-ring 50; a strain gage block 60; and a mounting block 70.

The inner diameter of split-ring 40 is large enough to permit the cylindrical body 100 of reservoir 10 to pass through the ring. But the larger diameter cover 102 does not. So the reservoir rests upon and is supported by the inner-split ring 40.

Strain gage block 60 is an I-beam shaped strain gage sensor which is attached by screws 72 at one end to the midpoint of split ring 40 and at the other end to mounting block 70. Mounting block 70 is a generally U-shaped member with a base portion 70a, two flange portions 70b, 70c and a ledge portion 70d.

Dowel pins 74 are used to secure the two pieces 50a and 50b of outer split-ring 50 to the respective flanges 70b and 70c of mounting block 70.

The base portion 70a is split by a key-hole 70e having an inner diameter large enough to accept a mounting structure, such as, IV pole 20. A bolt 76 extends through a transverse bore 78 in block 70 to an adjustment knob 79 which can be used to adjust the height of the reservoir in relation to the IV pole 30. Ledge portion 70d extends radially inwardly from the flanges and acts as a stop to prevent excessive radial rotation forces on reservoir 10 from being applied to the pole 20.

In operation, fluid from the wand 14 enters, ports 81, 82 or 85 depending on which is coupled by tubing 84, 82 or 80 to wand 14. Vacuum from a source (not shown) is coupled via tubing 140 to vacuum inlet port 120. The volume of fluid in reservoir 10 is sensed by its effect on the vertical strain imparted to the strain gage block 60. An analog electrical signal proportional to such strain is generated by the strain gage block 60 and is coupled over an electrical lead (not shown) to the cell salvage control electronics 18 (as shown in FIG. 1) for conversion to digital format and calibration to produce a volume signal representation of the instantaneous volume of fluid in the reservoir. The strain gage block 60 is preferably of the type made by Kulite Semiconductor Products, Inc. of Leona N.J. and sold as Gage Beam P/N BG14.

It is extremely sensitive to vertical forces applied to it but is substantially insensitive to horizontal forces. The outer split guard ring 50 supports the tubing 80, 82 and 84 to or from ports 81, 83 and 85 respectively and converts, or translates, any vertical force applied by such tubes into a horizontal force thereby preventing volume level misreadings by the sensor 30.

An advantage of this embodiment is that no modification has to be made to the standard reservoir since the sensor is totally extraneous to the reservoir.

Ultra-Sonic Sensor Embodiment

An ultrasonic sensor embodiment will now be described in connection with FIG. 2. Note that while FIG. 2 also shows a strain gage volume sensor 30 coupled between the pole 20 and reservoir 10 it is to be understood that for normal operation either one or the other embodiment would be employed, not both.

The ultrasonic sensor 11 is comprised of a piezoelectric crystal 210 which is acoustically coupled (placed in good acoustic contact) with a bottom surface of reservoir 10.

The crystal 210 is excited by an electrical pulse causing it to vibrate for a short period of time at its resonate frequency. The resulting sound wave is transmitted through the plastic surface at the bottom of the reservoir and into the fluid medium 212. At every boundary between two dissimilar mediums some sound energy is reflected; the greater the difference in acoustic impedance between the mediums the more energy reflected. Reflections near to the transducer from the plastic reservoir walls are filtered out by processor 16 and ignored. The sound energy travels through the fluid medium 212 until it is reflected off the fluid-air boundary 214 at the top of the fluid column. The reflected energy retraces its path back to the transducer 11 causing it to resonate the piezoelectric crystal 210 (now acting as a receiver) which creates a voltage signal which can be detected by the processor 16. The time delay between the transducer pulse and the detected reflection is a measure of the height of the boundary causing that reflection.

This height information is communicated from the processor to the control circuit 18 upon request. The control circuit uses this information (along with the known reservoir geometry) to calculate the volume of the fluid in the reservoir. This information is used in conjunction with software program logic to decide when to initiate processing of the fluid in the reservoir 10.

A fluid sensing chamber 216 is provided within the reservoir to channel the ultrasonic energy from transducer 210 and to isolate the contained fluid column 212 from fluid turbulence and an anti-foaming and particulate filter. Channeling the ultrasonic energy was found to improve the system tolerance to reservoir tilting by directing the reflected energy back to the transducer. In addition, the chamber isolates the ultrasonic signal path away from the reservoir filter. Otherwise, the reservoir filter would dissipate the ultrasonic signal by obstructing the energy pathway, scattering energy, absorbing energy, and providing a surface where air bubbles (energy scatterers) congregate. The fluid sensing chamber 216 isolates and protects the contained fluid from the fluid turbulence within the reservoir caused by reservoir filling. A slot 230 in the side of the fluid sensor chamber at the bottom allows fluid in and out of the chamber so that the level of fluid in the chamber matches the level of fluid in the reservoir.

In general the logic program for automation of the collection process comprises the following steps:

Power-on

After the cell salvage system with level sensor is turned on and the user initiates operation, the system begins monitoring the level (volume) of fluid in the reservoir 10. This involves interrogating the ultrasonic level sensor system or sampling the strain gage level sensor signal and processing the acquired sensor data to obtain a digital value which is related to the volume of fluid in the reservoir 10. This digital value is representative of fluid height when using the ultrasonic sensor system and of fluid weight in the strain gage sensor system implementation. From the digital value, using software logic, an estimate of the volume of fluid in the reservoir is calculated.

Initiating FILL

When a sufficient volume of fluid is present in the reservoir the system initiates the FILL cycle. This determination is made by comparing the digital value obtained by processing the sensor data to the digital value expected (target value) for a given reservoir volume. [In practice, one would wait until several successive samples exceed the target value before deciding that the target volume was reached. This or other means would be used to "filter" out noise due to disturbance of the reservoir.]The default volume for initiating FILL is preprogrammed. This is the "Start" level (for example 900 ml would be a default value for a 50 ml bowl.)

Resuming FILL After Emptying the Reservoir

At times the reservoir will be emptied during FILL before a full bowl of red blood cells advances the process into Wash. When this condition occurs the system will resume monitoring the level (volume) of fluid in the reservoir to determine when FILL can be resumed. The default level (volume) to resume FILL will be about one-half* (see note below) whatever the currently programmed "Start" level is. This is the "Resume" level. Using the resume target value, the decision-making process is the same as that described for initiating FILL. (For example, the default value of about 450 ml may be used as the resume level for a 250 ml bowl.)

Emptying the Bowl

Once the contents of the bowl have been washed and emptied the system will repeat the process above beginning with "Initiating Fill". As before, the FILL initiation level is reset to the "Start" level target.

User Modification

The user is able to modify the "Start" level of the level sensor via the system user interface (keypad, display, and software logic). The programmable FILL initiation range is 200 to 2500 ml. Once the "Start" level is chosen the "Resume" level will be some fraction i.e., one-half of the "Start" level or will be independently programmable.

Note: The value of "one-half" is not critical. Experience may show that a resume level which is two-thirds or three-fourths of the start level is better. Or experience may show that the resume level should be the same as the start level. Alternatively, the system may allow the user to independently program both the start and resume levels via the user interface. The actual values are not as important as the idea that the machine will automatically initiate processing when sufficient levels of fluid are available and before the reservoir overflows.

Figure 5:
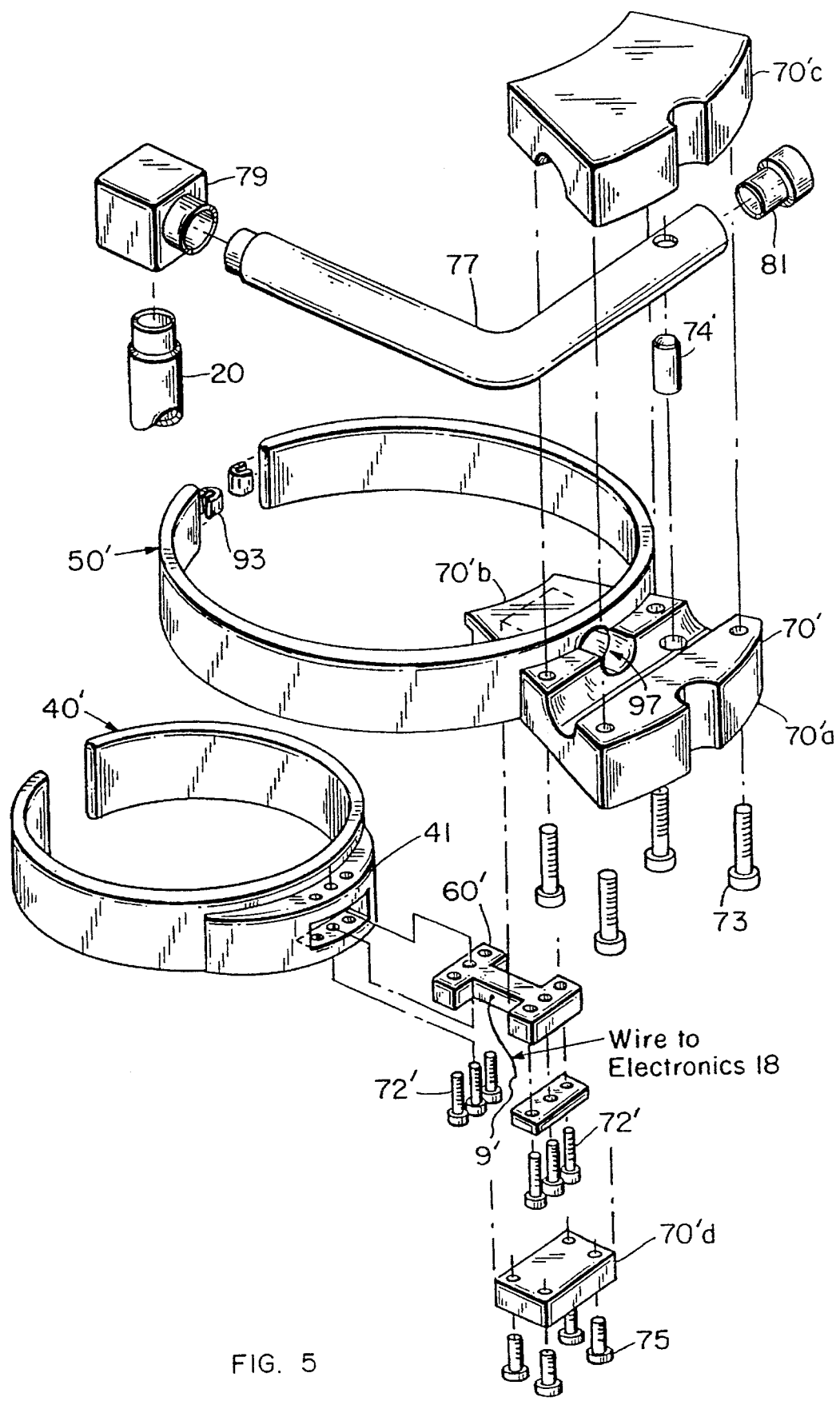
FIG. 5 is an exploded perspective view of an alternate strain gage assembly embodiment.

FIG. 5 depicts an alternate embodiment of the strain gage sensor of FIGS. 2–4 wherein among other things, the IV pole $20^1$ is off-set from the mounting block $70^1$. In FIG. 5 like ports carry the same reference numeral as in FIG. 4 with a prime suffix.

Sensor $30^1$ consists of an inner reservoir split-ring $40^1$; an outer reservoir split-ring $50^1$; a strain gage block $60^1$; and a mounting block $70^1$.

As in the previous embodiment the inner diameter of split-ring $40^1$ is large enough to permit the cylindrical body 100 of reservoir 10 to pass through the ring. The larger diameter cover 102 rests upon and is supported by the inner-spit ring $40^1$.

The strain gage block $60^1$ is attached by screws $72^1$ at one end to ring support number 41 welded to ring $40^1$ at the midpoint thereof. At the other end block $60^1$ is secured by screws $70^1$ to mounting block $70^1$. Mounting block $70^1$ is a generally pie-shaped member with an outer portion $70^1a$, an inner portion $70^1b$ and a clamp portion $70^1c$, The outer portion $70a$ has a circumferential groove $70e$ formed therein to accept horizontal IV pole segment 77 with the segment 75 pinned in place by drive pin 74, clamp $70^1c$may be affixed to portion $70'a$ by screws 73. A ledge on inner portion $70^1b$ extends radially inwardly from the flanges. An overload protective block $70^1d$ is affixed to the ledge and acts as a stop to prevent excessive radial rotation forces on reservoir 10 from being applied to the pole 20. End cap 81 encloses an end of segment 77 while knuckle 79 encloses the other end. Color coded balls 93 are provided at each end of the split outer ring to indicate which color-coded tubing line attaches to the reservoir. Wire $9^1$ is coupled through radial bore 97 to control electronics 18.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. In an extracorporeal system for the recovery and washing of salvaged blood collected from a surgical site of a patient the improvement comprising:

a) a reservoir for storing the collected blood;

b) a sensor for periodically sensing the volume of the salvaged blood stored in the reservoir and generating a volume signal, the sensor being substantially insensitive to forces in a horizontal direction;

c) a blood cell salvaging system fluidly coupled to said reservoir for processing the salvaged blood; and d) a control apparatus, which, in response to the volume signal, initiates or terminates processing of said salvaged blood.

2. The system of claim 1 wherein the volume sensor is a strain gage transducer.

3. An extracorporeal system for the recovery and washing of salvaged blood collected from a surgical site of a patient comprising:

a) a reservoir for storing the collected blood, the reservoir having tubing associated therewith and extending therefrom, the tubing being subject to vertical forces during system operation:

b) a radially inner support member for supporting the reservoir;

c) a radially outer support member secured to a mounting surface; and d) a strain gage coupled between said inner support member and outer support member for sensing vertical strain forces therebetween and converting vertical forces originating with the tubes into horizontal forces.

4. The system of claim 3 wherein the inner and outer member are formed in the shape of a split-ring.

5. The system of claim 4 wherein the reservoir is formed of a tubular body having a maximum diameter D1 with a cover having a diameter D2 and wherein the diameter of the inner member is larger than D1 and smaller than D2 such that the reservoir may be suspended on the inner member solely by the cover.

6. The system of claim 4 wherein the outer member prevents tubing, coupling the reservoir to other items, from exerting a vertical strain on the strain gage.

7. A system for processing of shed blood comprising:
   a) a suction wand for suctioning the shed blood;
   b) a reservoir for storing and filtering the shed blood;
   c) apparatus for processing the stored and filtered shed blood to concentrate, wash and collect components of the shed blood; and
   d) a strain gage sensor for sensing the volume of shed blood in the reservoir and generating a volume signal indicative thereof, the sensor being substantially insensitive to horizontal forces; and
   e) control means responsive to said volume signal for controlling the operation of said apparatus.

8. The system of claim 7, in which the apparatus for processing the shed blood is a centrifuge which separates the whole blood into components.

* * * * *